United States Patent
Spilgies

(10) Patent No.: US 9,616,212 B2
(45) Date of Patent: Apr. 11, 2017

(54) IMPLANT CANNULA HAVING AN IMPLANT AND A METHOD FOR SECURING IMPLANTS IN AN INJECTION CANNULA

(75) Inventor: Heiko Spilgies, Munich (DE)

(73) Assignee: LUYE PHARMA AG, Miesbach (DE)

( * ) Notice: Subject to any disclaimer, the term of this patent is extended or adjusted under 35 U.S.C. 154(b) by 509 days.

(21) Appl. No.: 13/637,672

(22) PCT Filed: Feb. 17, 2011

(86) PCT No.: PCT/EP2011/000763
§ 371 (c)(1),
(2), (4) Date: Nov. 26, 2012

(87) PCT Pub. No.: WO2011/120608
PCT Pub. Date: Oct. 6, 2011

(65) Prior Publication Data
US 2013/0110077 A1    May 2, 2013

(30) Foreign Application Priority Data

Apr. 1, 2010 (DE) .......................... 10 2010 013 898

(51) Int. Cl.
| | | |
|---|---|---|
| *A61M 37/00* | (2006.01) | |
| *A61K 38/09* | (2006.01) | |
| *A61L 29/06* | (2006.01) | |
| *A61L 29/16* | (2006.01) | |
| *A61B 17/34* | (2006.01) | |

(52) U.S. Cl.
CPC .......... *A61M 37/0069* (2013.01); *A61K 38/09* (2013.01); *A61L 29/06* (2013.01); *A61L 29/16* (2013.01); *A61B 17/3468* (2013.01); *A61L 2300/40* (2013.01)

(58) Field of Classification Search
CPC .. A61K 38/00; A61K 9/0024; A61B 17/3468; A61M 37/0069
USPC ............. 604/57, 59–62, 64, 93.01, 506; 424/422–437; 606/92–94
See application file for complete search history.

(56) References Cited

U.S. PATENT DOCUMENTS

| | | | |
|---|---|---|---|
| 4,787,384 A | 11/1988 | Campbell et al. | ............ 606/117 |
| 5,002,548 A | 3/1991 | Campbell et al. | ............ 606/116 |
| 6,402,677 B1 | 6/2002 | Jacobs | ............... 600/7 |
| 2005/0131386 A1* | 6/2005 | Freeman et al. | ............... 604/522 |
| 2007/0233146 A1* | 10/2007 | Henniges | ........... A61B 17/3472 606/91 |
| 2007/0292473 A1 | 12/2007 | Cheikh | ......................... 424/426 |
| 2008/0033351 A1 | 2/2008 | Trogden | ........................... 604/57 |
| 2008/0294039 A1* | 11/2008 | Jones | ................ A61M 37/0069 600/431 |
| 2009/0047327 A1* | 2/2009 | Eaton | ................... A61K 9/0024 424/434 |
| 2009/0124998 A1* | 5/2009 | Rioux | ................... A61M 5/329 604/506 |

FOREIGN PATENT DOCUMENTS

| | | |
|---|---|---|
| DE | 69823390 T2 | 8/2004 |
| DE | 10 2005 020078 A1 | 11/2006 |
| EP | 1300173 A2 | 4/2003 |

OTHER PUBLICATIONS

International Search Report from PCT/EP2011/000763, Apr. 12, 2011.
Office Communication dated Jul. 22, 2016 from corresponding Canadian Application No. 2,790,257 filed Feb. 17, 2011.

* cited by examiner

*Primary Examiner* — Kevin C Sirmons
*Assistant Examiner* — Amber Stiles
(74) *Attorney, Agent, or Firm* — Licata & Tyrrell P.C.

(57) ABSTRACT

The application provides an injection cannula having an implant which is detachably secured in the cannula. The application also provides a method for detachably securing an implant in an injection cannula.

23 Claims, No Drawings

IMPLANT CANNULA HAVING AN IMPLANT AND A METHOD FOR SECURING IMPLANTS IN AN INJECTION CANNULA

This application is the national phase under 35 U.S.C. §371 of PCT International Application No. PCT/EP2011/000763, filed Feb. 17, 2011, which claims priority from DE 10 2010 013 898.3, filed Apr. 1, 2010, the contents of which are incorporated herein by reference in their entireties.

The present invention relates to an injection cannula having an implant and to a method for detachably securing an implant in an injection cannula.

In modern pharmacotherapy, for example in the case of long-term treatment of diseases, there are used implantable medicament depots which are also referred to as implants. Implants frequently contain a pharmaceutical product (medicament or active ingredient) in a matrix made of a biologically degradable plastics material. The implants, which are preferably in the form of small cylindrical rods made of the plastics/active ingredient matrix, are preferably subcutaneously injected into a patient. The implant breaks down in the patient's body, for example as a result of hydrolysis of the plastics matrix due to the natural water balance in the human body, with the result that the active ingredient enclosed in the plastics matrix or bonded thereto is released in a controlled way in vivo and administered to the patient over a prolonged period (depot function). The period over which the medicament is released in the patient's body typically extends over several weeks to months, for example over four to six weeks. Implants are used, for example, in the treatment of tumour patients, the implant releasing in the patient's body an active ingredient which, for example, causes a lowering of testosterone and thus inhibition of tumour growth. An example of an active ingredient administered in the form of an implant is goserelin.

In general, the implant is introduced into the human body using an implantation device. Such an implantation device usually consists of three main functional parts: an injection cannula, an active ingredient container or cannula holder, which can be permanently connected to the cannula, and an applicator, for example in the form of a plunger, with which the implant can be introduced into the tissue of the patient through the injection cannula. In a customary embodiment the active ingredient container or cannula holder contains a plunger channel by way of which the plunger is guided directly into the cannula. Such implantation devices are known.

In order to ensure the sterility of the implant and the implantation device, implantation devices are often filled with an implant under sterile conditions by the manufacturer, and the filled implantation device is then sterile-packed. It has been found in practice that it is essential to prevent an implant from accidentally dropping out from the implantation device, for example in the course of unpacking, moving, handling or positioning. Various safety elements for implantation devices have been developed for that purpose.

For example, U.S. Pat. No. 4,787,384 A describes an implantation device in which an implant is held firmly in the plunger channel (active ingredient container) by a projection provided at the proximal end of the plunger channel (that is to say at the end of the plunger channel connected to the cannula). Applying sufficient force to the plunger overcomes the friction between the implant and the projection, and the implant is moved into the cannula and then injected. This implantation device with a projection has the disadvantage that an implant made of a brittle plastics/active ingredient matrix can break when the force required is applied. For that reason GB 786,850 A and EP 631 794 A1, for example, propose firmly holding an implant in the plunger channel by means of resiliently pretensioned retaining elements arranged at the proximal end of the plunger channel, the retaining elements being so flexible that they give way to the implant when force is applied to the plunger and free up the plunger channel.

All those implantation devices in which the implant is held in the plunger channel (active ingredient container) must, as a functional necessity, have a plunger that is long enough to inject the implant out of the plunger channel through the entire length of the cannula. An implantation device having such a long plunger is problematic to handle and use.

In order to avoid an implantation device having a long plunger, in accordance with EP 1 716 883 A1 and DE 20 2009 016 524 U1 the implant is firmly held in the cannula itself. EP 1 716 883 A1 describes a sleeve having a channel running therein and a retaining element resiliently pretensioned in the channel transversely with respect to its longitudinal axis, it being possible for the sleeve to be pushed over an injection cannula having a lateral opening (for example, a pencil point cannula) and for an implant located in the cannula to be clamped at that location. As a result of the use of the sleeve it is possible to use an implantation device having a plunger which need only be long enough to inject the implant out of the cannula. In DE 20 2009 016 524 U1 instead of a sleeve an O-ring made of a resilient material such as, for example, rubber is used to clamp an implant in a cannula having a lateral opening at that location. A problem is that both the sleeve in accordance with EP 1 716 883 A1 and the O-ring in accordance with DE 20 2009 016 524 U1 can be displaced by the user, with the result that the implant is released and is able to slide in the cannula or possibly even drop out from the cannula altogether. In addition, the sleeve and the O-ring respectively completely and partially cover over the lateral opening of the cannula, thereby making it difficult to make a visual check for the presence of an implant in the cannula.

EP 1 716 883 A1 also describes a method of securing an implant in which an implant in the form of a small rod is introduced using tweezers into the proximal opening of a cannula and fixed in place with a solution of the plastics material from which the implant is also made, the plastics solution being applied to the implant in the form of metered droplets likewise by way of the proximal opening of the cannula. The plastics droplet sits proximally in front of the small implant rod and adheres both to the inner wall of the cannula and to the small implant rod and cures at room temperature. When the implant is administered by means of the plunger, the plastics droplet is detached and releases the implant. A disadvantage of this method is that it is not possible to ensure a reproducible position of the droplet, and thus of the implant, in the cannula. In addition, important properties of the implant, such as, for example, the release of active ingredient, may be affected, in that the surface of the implant is irregularly enlarged or changed in some other way, because the implant may start to be dissolved by the plastics solution. For example, the surface of the small implant rod by way of which the active ingredient is to be released may also be changed to different degrees by the plastics solution, with the result that parts of the surface may have only limited availability for the release of the active ingredient from the small implant rod, which may have an adverse effect on the uniformity and/or duration of active ingredient release. Furthermore, the partial dissolution may weaken the structure of the implant, so that the implant can break during injection.

The problem of the present invention is to improve on the prior art.

Accordingly, the invention provides an injection cannula having an implant, the implant being detachably secured in the injection cannula over part of at least one longitudinal side with at least one physiologically tolerable material. The injection cannula with implant according to the invention ensures that the implant remains reliably in the injection cannula when the cannula is moved, for example in the course of transport, unpacking, handling, positioning etc., but is easily released when an applicator of an implantation device, for example a plunger or the like, acts in the intended manner on the implant, with the result that the implant is injected out of the cannula into a patient. The injection cannula with implant according to the invention accordingly also ensures that the implant is not only sterile at the time of injection but is also unchanged, that is to say still meets all the approval requirements under the laws governing pharmaceuticals without being changed by interactions with fixing materials or the environment.

The invention also provides a method of releasably securing an implant in an injection cannula in which a flowable physiologically tolerable material is introduced into the cannula before an implant is introduced into the cannula.

As understood by this invention, an implant is a customary implant or an implantable medicament depot which can be used in medicament therapy for the long-term treatment of diseases. An implant includes a pharmaceutical product (medicament or active ingredient).

Preferred active ingredients are psychopharmaceuticals, especially antischizophrenics, such as, for example, risperidone, or peptides or proteins. An implant especially includes an active ingredient from the group of hormones or hormone antagonists and agonists, for example LHRH or LHRH antagonists, such as anastrozole. Also preferred are goserelin, leuprorelin and octreotide.

The active ingredient is preferably enclosed in a matrix or bonded thereto. The matrix consists preferably entirely of physiologically tolerable materials which, after release of the active ingredient from the implant, either remain in the body or can be removed from the body, or which are degraded or absorbed in the body during or after release of the active ingredient.

Preferred examples of matrix materials are polymers, copolymers and lipids. The matrix especially comprises a biologically degradable plastics material. Preferred examples of biologically degradable plastics materials suitable as matrix materials include polymers and copolymers of lactic acid and/or glycolic acid, especially polylactides and poly-lactide-co-glycolides. Further preference is given to polyesters. Special preference is given to biologically degradable plastics materials which, by virtue of the natural water balance in the human body, can be degraded by hydrolysis once the implant has been injected into the patient, preferably subcutaneously. As a result, the active ingredient enclosed in the plastics matrix or bonded thereto is released in a controlled way in vivo and delivered to the patient over a prolonged period (depot function). Preferred examples of plastics materials biologically degradable by hydrolysis are polylactides and poly-lactide-co-glycolides, and also polyesters and lipids. Especially preferred implants comprise a plastics/active ingredient combination of poly-lactide-co-glycolide and goserelin.

An implant can have any customary shape. Suitable shapes of implant are cylindrical or the like. Preferably an implant is in the form of a small cylindrical rod made of the plastics/active ingredient matrix. Such an implant can preferably be produced, for example, by extrusion. Alternatively an implant can be spherical, for example in the form of a pellet, or the like.

Preferred dimensions of an implant are a length of from 5 to 25 mm, preferably from 10 to 20 mm, and a cross-section of from 0.8 to 2.5 mm, preferably from 1.1 to 1.6 mm. An implant preferably includes from 0 to 50% by weight, especially from 5 to 40% by weight, and more especially from 15 to 30% by weight, of active ingredient and from 50 to 100% by weight, especially from 60 to 95% by weight, and more especially from 70 to 85% by weight, of biologically degradable plastics material. Preferably, the total mass of the implant is from 10 to 100 mg, especially from 15 to 75 mg, and more especially from 20 to 50 mg.

In an especially preferred embodiment, a small-rod-shaped implant having dimensions of from 12 to 16 mm length and from 1.05 to 1.25 mm diameter comprises from 3.5 to 3.8 mg of goserelin and from 15 mg to 25 mg of biologically degradable polymer, preferably poly-lactide-co-glycolide. That implant is preferably suitable as a one-month formulation. In another especially preferred embodiment a small-rod-shaped implant having dimensions of from 17 to 25 mm length and from 1.40 to 1.60 mm diameter comprises from 10.6 to 11.0 mg of goserelin and from 35 mg to 55 mg of biologically degradable polymer, preferably poly-lactide-co-glycolide. That implant is preferably suitable as a three-month formulation. Those implants can also comprise alternative or additional active ingredients, such as, for example, leuprorelin and/or octreotide, it being possible to adapt the respective dosages accordingly.

An injection cannula as understood by this invention is any customary injection cannula which can be used in the field for the injection of implants. A cannula is preferably produced from special steel, the surface especially being siliconised. A cannula preferably has a length of from 20 mm to 50 mm, especially from 25 mm to 40 mm, and more especially from 30 mm to 34 mm, an external diameter of from 1.0 mm to 3.0 mm, especially from 1.5 mm to 2.5 mm, more especially from 1.8 mm to 2.0 mm, and an internal diameter of from 0.8 mm to 2.8 mm, especially from 1.3 mm to 2.3 mm, and more especially from 1.6 mm to 1.8 mm. The wall thickness of the cannula is preferably about 0.2 mm. Special preference is given to a cannula having a length of from 30 to 34 mm and an internal diameter of 1.4 mm and an external diameter of 1.6 mm for an implant suitable as a one-month formulation, and a cannula having a length of from 30 to 34 mm and an internal diameter of 1.8 mm and an external diameter of 2.0 mm for an implant suitable as a three-month formulation.

A cannula preferably has a customary connecting means for connecting the cannula to an application device. Examples of suitable connecting means are a "luer-lock system" or the like. The term "cannula" is used for the injection needle alone as well as for the injection needle with the connecting means (needle holder).

The internal diameter of the injection cannula is greater than the external diameter of the implant. Preferably, the difference between the internal diameter of the injection cannula and the external diameter of the implant is from 0.1 mm to 0.8 mm, especially from 0.2 mm to 0.5 mm, and more especially from 0.3 mm to 0.4 mm. In a preferred embodiment, an implant having a diameter of about 1.15 mm is used in combination with an injection cannula having an internal diameter of 1.4 mm.

According to the invention the implant is detachably secured in the injection cannula with at least one physiologically tolerable material. "Physiologically tolerable material" as understood by the invention means that a material has no adverse effects on a living organism (patient), especially when introduced into the body of the patient, especially by subcutaneous injection. Suitable physiologically tolerable materials are selected from biologically inert materials and biologically degradable materials, especially physiological materials or biologically degradable polymeric materials the monomers of which are physiological.

The at least one physiologically tolerable material is preferably a material different from the material included in the implant. In other words, the implant does not include any material identical to the physiologically tolerable material. Preferably the at least one physiologically tolerable material also does not comprise any material which could enter into interaction with the materials of the implant. The physiologically tolerable material especially does not comprise any material which could cause one or more of the materials of the implant to start to dissolve and/or break down. For example, the physiologically tolerable material preferably does not comprise any material which could cause the active ingredient and/or the matrix polymer material of the implant to start to dissolve and/or break down, and/or could cause the implant to swell. The physiologically tolerable material also preferably does not comprise any material which could enter into a reaction with one or more of the materials of the implant.

The physiologically tolerable material preferably adheres to the implant less strongly than to the material of the inner wall of the cannula. For example, the physiologically tolerable material adheres more strongly to the surface of the inner wall of the cannula than to the surface of the implant.

Preferred examples of inert materials are polymer materials or plastics materials based on carbon, such as, for example, polyethylene glycols, especially polyethylene glycols having a molecular weight of from 400 to 1000, perfluorinated polymers, such as, for example, polytetrafluoroethylene (Teflon), polyacetals, such as, for example, polyoxymethylene (POM), carbon/silicon-based plastics materials, such as, for example, silicones, especially rubber-like silicone masses which can also include perfluorinated groups or the like, or the like.

Preferred examples of biologically degradable materials are physiological materials, such as, for example, triglycerides, diglycerides, monoglycerides, fatty acids, fatty alcohols, or the like.

Preferably, a physiologically tolerable material is selected from one or more semi-solid materials and/or one or more cured materials.

A semi-solid material preferably denotes, as understood by this invention, a material having a viscosity of 90 cP or more. Examples of a semi-solid material are viscous polymers, such as, for example, polyethylene glycols having a molar weight of from 400 to 1000, such as PEG 400, PEG 700 and PEG 1000, and also mixtures thereof, and ointment-like masses (creams), such as, for example, emulsions, comprising triglycerides, fatty acids, fatty alcohols, and mixtures thereof, and the like. Especially preferred examples are tristearate, tripalmitate, stearic acid, palmitic acid, stearyl alcohol, palmityl alcohol.

The semi-solid material can also comprise suitable additives which are known in the field of ointment and cream manufacture, such as, for example, suitable solvents, plasticisers, stabilisers, emulsifiers, or the like.

A cured material preferably denotes, as understood by this invention, a material which can be processed, for example introduced into the cannula, in the flowable state, and then becomes solid or is converted into the solid state. Examples of such materials are, for example, solutions, such as, for example, rubber solutions, sugar solutions and the like, suspensions, such as, for example, rubber- or plastics-latex suspensions, and the like, which become solid on drying; and also solutions or mixtures of suitable monomers, oligomers, and the like, which become solid by polymerisation; and the like. The term "cured material" also includes a polymer material which is flowable in the molten state, and becomes solid on cooling, such as, for example, customary melt adhesives.

The physiologically tolerable material preferably comprises a polymer material. Examples of a semi-solid polymer material are viscous polymers, such as, for example, polyethylene glycols having a molar weight of from 400 to 1000, such as PEG 400, PEG 700 and PEG 1000, and also mixtures and copolymers thereof, such as, for example, mixtures of PEG and polypropylene glycol (PPG) and PEG-PPG copolymer, and the like.

Examples of a cured polymer material is a customary polymer material, the term polymer material including both polymers and copolymers. Preferred polymers and copolymers are perfluorinated polymers, such as, for example, polytetrafluoroethylene (Teflon), polyacetals, such as, for example, polyoxymethylene (POM), carbon/silicon-based polymers, such as, for example, silicones, especially rubber-like silicone masses, which may also include perfluorinated groups and the like, and the like, and copolymers and polymer mixtures containing them, and the like.

The cured polymer material is especially an elastomeric polymer. Examples of elastomeric polymers are natural and synthetic rubbers.

The implant is detachably secured in the injection cannula over at least part of at least one longitudinal side. "Detachably secured" means here that the implant is normally firmly held securely in an injection cannula, but is easily released by the application of customary force when an applicator guided through the cannula is used as intended. "Firmly held" as understood by the invention means that the implant remains at its location in the cannula when the cannula is moved, such as, for example, in the course of transport, unpacking, handling, positioning and the like, but is easily released when an applicator of an implantation device, for example a plunger or the like, acts in the intended manner on the implant, with the result that the implant is injected out of the cannula into a patient. The force required to expel or inject the implant from the injection cannula must not be so great that the implant breaks. According to the invention, the implant is preferably detachably secured or firmly held in the injection cannula only by friction, the corresponding friction force being provided, for example, by the degree of wetting and the viscosity of a semi-solid material or by the adhesion force of a cured material, or the like.

"Detachably secured" does not mean that the implant is permanently secured in the cannula, for example by being adhesively bonded with a suitable adhesive, plastics material or the like, even if such a securing means can possibly also be pressed out of the cannula on application of increased force using an applicator acting in the intended manner, even if the implant breaks in the process.

According to the invention the implant is detachably secured in the injection cannula over at least part of at least one longitudinal side, and the implant is preferably secured in the injection cannula over at least part of one or two longitudinal sides, and the implant is especially detachably secured in the injection cannula over at least part of precisely one longitudinal side. As understood by the invention, longitudinal side of the implant refers to each side of the implant which is arranged parallel to the main axis of the cannula when the implant is located in the cannula. An implant in the form of a small cylindrical rod accordingly has only one longitudinal side, while an implant having a square cross-section has four longitudinal sides and an implant having a hexagonal cross-section has six longitudinal sides, etc. In an implant having an angled cross-section, a longitudinal side can also be in the form of a longitudinal edge between two adjacent longitudinal sides. An implant having an angled cross-section can preferably be detachably secured in the injection cannula over a longitudinal edge.

The implant can be detachably secured in the injection cannula over the entire surface of the at least one longitudinal side, or over part of the surface area of the at least one longitudinal side. Preferably the implant is detachably secured in the injection cannula over 50% or less of the at least one longitudinal side, especially over 30% or less, more especially over 20% or less and very especially over 10% or less. In a preferred embodiment, a cylindrical implant is detachably secured in the injection cannula over at least one annular region of the surface of its longitudinal side. The annular region preferably comprises 50% or less of the surface of the longitudinal side of the cylindrical implant, especially 30% or less, more especially 20% or less, very especially 10% or less, and especially preferably 5% or less.

In another preferred embodiment, the implant is detachably secured in the injection cannula over at least one point on the surface of at least one longitudinal side. The implant is preferably mounted in the injection cannula over one or more, preferably two, three, or four, points. As understood by the invention, a "point" is a region of the surface of a longitudinal side of the implant. A point preferably has a surface area of 10 mm$^2$ or less, especially 5 mm$^2$ or less, more especially from 0.001 to 2 mm$^2$, and very especially from 0.01 to 1 mm$^2$. Preferably, a plurality of points are arranged in a ring on the surface of the implant.

The implant is detachably secured in the injection cannula with at least one physiologically tolerable material over at least one longitudinal side. Accordingly, the at least one physiologically tolerable material is arranged between the surface of at least one longitudinal side of the implant and the surface of the inner wall of the cannula. The at least one physiologically tolerable material preferably has a layer thickness of from 0.1 to 1.2 mm, especially from 0.2 to 1.0 mm, and more especially from 0.3 to 0.8 mm.

In an especially preferred embodiment, the injection cannula has a lateral opening. Such injection cannulas are commercially available, for example under the designation "pencil point cannula", for example from the company Süddeutsche Feinmechanik. A preferred cannula made of special steel with a luer-lock connecting system has a length of 32 mm, an external diameter of 1.6 mm and an internal diameter of 1.4 mm, an opening having a diameter of 1.2 mm being formed at a distance of 26 mm from the tip of the cannula. Such cannulas are already used for implant systems (see, for example, EP 1 716 883 A1 and DE 20 2009 016 524 U1, so that in the case of the present invention it is readily possible to use existing systems. The costs required for new development therefore do not arise.

The implant is especially arranged in the region of the lateral opening of the injection cannula. In this arrangement the lateral opening allows a simple visual check for the presence of an implant in the cannula.

In an especially preferred embodiment of the injection cannula with implant according to the invention, the implant is detachably secured in the injection cannula, in the region of a lateral opening of the injection cannula, over at least one longitudinal side with a physiologically tolerable material on the inner wall of the cannula which is located opposite the lateral opening. Preferably, the implant is then secured in the injection cannula in the region of the lateral opening of the injection cannula over precisely one point, on the inner wall of the cannula which is located opposite the lateral opening.

In an alternative preferred embodiment of the injection cannula with implant according to the invention, the implant is detachably secured in the injection cannula in the region of a lateral opening of the injection cannula over at least one longitudinal side with at least one physiologically tolerable material on the inner wall of the cannula which is arranged below and/or above the lateral opening relative to the main axis of the cannula. Preferably, a cylindrical implant is detachably secured in the injection cannula over at least one annular region of the surface of its longitudinal side on the inner wall of the cannula, the annular region being arranged below and/or above the lateral opening relative to the main axis of the cannula. In an especially preferred embodiment, the annular region is arranged below the lateral opening of the cannula, that is to say between the lateral opening and the proximal end of the cannula (sharp end or injection opening of the cannula).

Furthermore, the invention provides a method for detachably securing an implant in an injection cannula in which a flowable physiologically tolerable material is introduced into the cannula before an implant is introduced into the cannula. Detachably securing as understood by the invention means that an implant so secured is firmly held reliably in the cannula, that is to say remains reliably at its location in the cannula, when the cannula is moved, such as, for example, in the course of transport, unpacking, handling, positioning and the like, but is easily released when an applicator of an implantation device, for example a plunger or the like, acts in the intended manner on the implant, with the result that the implant is injected out of the cannula into a patient.

A flowable physiologically tolerable material as understood by the invention is any customary flowable physiologically tolerable material known in the field. Flowable as understood by the invention means that the material is able to flow under customary processing conditions, so that it can be processed in the same way as a fluid. Customary processing conditions are preferably temperatures of from 0 to 100° C., preferably from 20 to 80° C., and especially room temperature (25° C.), under an oxygen-containing atmosphere, preferably air.

The flowable physiologically tolerable material can comprise a single substance or a mixture of two or more substances. Preference is given to the inert and biologically degradable materials mentioned above which can be used singly or in admixture. The flowable physiologically tolerable material can furthermore also comprise suitable additives known in the field, such as, for example, suitable solvents, plasticisers, stabilisers, emulsifiers, or the like.

Especially preferred flowable physiologically tolerable materials are triglycerides, fatty acids, fatty alcohols, especially of stearate and palmitate, phospholipids, various grades of PEG, for example PEG 400, and the like.

Examples of curable flowable physiologically tolerable materials are flowable physiologically tolerable materials that comprise volatile constituents, such as, for example, solvents or the like, or flowable physiologically tolerable materials that undergo a reaction in the cannula, such as, for example, curable polymers, or the like. Preferred examples are silicone rubbers, such as, for example, RTV-1 silicone rubbers, such as, for example, Elastosil E41 from Wacker Chemie.

The method according to the invention requires the flowable physiologically tolerable material to be introduced into the cannula before an implant is introduced into the cannula. The introduction of the flowable physiologically tolerable material can be effected using any customary technique. Preferred examples thereof are introduction using an application device, especially metered introduction using a suitable metering device.

The amount of flowable physiologically tolerable material to be introduced can readily be determined by the person skilled in the art in accordance with the selected dimensions of the cannula and implant. As a rule, the objective will be to introduce as small as possible an amount of the flowable physiologically tolerable material into the cannula. Depending upon the flowable physiologically tolerable material used, preferably less than 25 μl are introduced into the cannula, especially less than 15 μl, more especially less than 5 μl, and very especially less than 1 μl. In another embodiment, depending upon the flowable physiologically tolerable material used, preferably less than 25 mg are introduced into the cannula, especially less than 15 mg, more especially less than 5 mg, and very especially less than 1 mg. It is also possible, however, first to introduce a relatively large amount of the flowable physiologically tolerable material into the cannula and later to remove a portion thereof in a second step before the implant is introduced into the cannula.

The undesired material can also, for example, be removed in the flowable state. For example, the entire cannula can in a first step be filled with the flowable physiologically tolerable material, for example by closing the cannula at the lower end with the cannula arranged vertically, and then allowing the flowable physiologically tolerable material to flow out of the cannula, for example by opening the lower end, with the result that only the inner walls of the cannula remain wetted. Depending upon the flowable physiologically tolerable material used, the material can flow out solely under gravity or with the assistance of suitable means, such as, for example, a stream of gas, for example compressed air, suitable tools, such as, for example, plungers, stylets, or the like. In another example, the flowable physiologically tolerable is allowed to solidify in the cannula, for example by evaporation of a solvent it contains, solidification by cooling, curing or polymerisation, or the like, before the undesired material is removed from the cannula using suitable means, such as, for example, a stream of gas, for example compressed air, suitable tools, such as, for example, plungers, stylets, or the like, before the implant is introduced into the cannula, preference being given to the use of a plunger, stylet or the like, the diameter of the plunger or stylet being smaller than the diameter of the implant.

For the introduction of the flowable physiologically tolerable material into the injection cannula there is preferably used a suitable application device, such as, for example, an application cannula, a capillary or the like, with which the flowable physiologically tolerable material can advantageously be introduced into the injection cannula at a specific location. An application cannula or capillary preferably has dimensions, such as, for example, length, external diameter, and the like, that allow it to reach any desired location inside the injection cannula and to effect metered introduction of the flowable physiologically tolerable material at that location.

Introducing the flowable physiologically tolerable material before the introduction of the implant has the advantage that a flowable physiologically tolerable material can also be introduced into the cannula under conditions which are harmful to the implant or the active ingredient contained therein. For example, it is possible to use a flowable physiologically tolerable material which is flowable only at elevated temperatures or which comprises a substance which adversely affects or changes the implant or the active ingredient, such as, for example, a solvent which can also dissolve or break down the implant or the active ingredient itself. It is accordingly possible to use materials which, although distinguished by good properties, such as, for example, physiological tolerability, flowability, meterability under flow conditions, processability, storability, stability and the like, cannot be processed under conditions which are compatible with the implant or the active ingredient contained therein.

In the last step of the method according to the invention, the implant is introduced into the cannula. The implant can be introduced into the cannula from the tip of the cannula (the proximal end) or from the end of the connecting device (the distal end). Preferably, the implant is introduced into the cannula from the distal end, it being possible to use a suitable tool, such as, for example, a tool for introducing the implant into the cannula, a tool for positioning the implant in the cannula, and the like.

All the steps of the method according to the invention can be carried out under sterile conditions. Alternatively, the first step of introducing the flowable physiologically tolerable material, as well as optional intermediate steps for curing, processing, partial removal, etc. thereof, can take place under non-sterile conditions and the injection cannula with the introduced material can then be sterilised before the implant is introduced into the cannula under sterile conditions. Also, introduction and packaging can take place under non-sterile conditions and the packaged device can be sterilised subsequently. Suitable sterilisation methods are heat sterilisation, moist air sterilisation and, especially, sterilisation with gamma radiation (gamma sterilisation). All the steps can preferably be automated.

The method according to the invention has the result that an implant is firmly held in an injection cannula. "Firmly held" as understood by the invention means that the implant remains at its location in the cannula when the cannula is moved, such as, for example, in the course of transport, unpacking, handling, positioning and the like, but is easily released when an applicator of an implantation device, for example a plunger or the like, acts in the intended manner on the implant, with the result that the implant is injected out of the cannula into a patient. The method according to the invention ensures that the implant is not only sterile at the time of injection but is also unchanged, that is to say still meets all the approval requirements under the laws governing pharmaceuticals without being changed by interactions with fixing materials or the environment.

As a result of the material introduced, the internal diameter of the injection cannula is made narrower. As a result, the free movement of the implant in the injection cannula is impeded and the implant is firmly held in the cannula. By controlling the amount of material introduced and the site of introduction thereof, the internal diameter of the cannula can be made narrower everywhere or only at some locations. Preferably, the internal diameter is made narrower only at some points. For example, the internal diameter can be made narrower at one location by means of one or more, preferably one, two, three, four, or more, droplets of the introduced material. Special preference is given to one-point narrowing. Alternatively, the internal diameter can be made narrower by a circumferential ring of introduced material.

Preferably, the flowable physiologically tolerable material is selected from a semi-solid material or a curable polymer material. A semi-solid material as understood by this invention denotes a material having a viscosity of 90 cP or more. Examples of a semi-solid material are viscous polymers, such as, for example, polyethylene glycols having a molar weight of from 400 to 1000, such as PEG 400, PEG 700 and PEG 1000, and also mixtures thereof, or mixtures of liquid and solid polyethylene glycols, such as, for example, PEG 300 and PEG 1500 or PEG 400 and PEG 1000, in each case in a ratio of 1:1, and ointment-like masses (creams), such as, for example, emulsions, comprising triglycerides, fatty acids, fatty alcohols, and mixtures thereof, and the like. The semi-solid material can also comprise suitable additives which are known in the field of ointment and cream manufacture, such as, for example, suitable solvents, plasticisers, stabilisers, emulsifiers, or the like.

A curable polymer material is a customary polymer material for the production of polymers or copolymers, such as, for example, a mixture of suitable monomer and hardener, or a mixture of suitable hardener and oligomers, or the like. The curable polymer material can comprise customary additives, such as, for example, solvents, and the like. Preferred polymers are perfluorinated polymers, such as, for example, polytetrafluoroethylene (Teflon), polyacetals, such as, for example, polyoxymethylene (POM), carbon/silicon-based polymers, such as, for example, silicones, especially rubber-like silicone masses, which may also include perfluorinated groups and the like, and copolymers and mixtures thereof, and the like. Special preference is given to silicone rubbers.

Preferably, a polymer material is introduced into, the cannula and cured before the implant is introduced into the cannula. Curing as understood by this invention means that the flowable polymer material is converted into a corresponding polymer by a polymerisation reaction. A cured polymer can be processed in an optional intermediate step before the implant is introduced into the cannula. For example, undesired cured polymer can be removed using a suitable tool, such as, for example, a stylet or the like.

In an especially preferred embodiment, one or more, preferably two, three, or four, points of elastomeric polymer are applied to the inner wall of an injection cannula. Preferably, a plurality of points are applied in a ring to the inner wall of the cannula. Alternatively, it is also possible for a circumferential ring of elastomeric polymer to be applied to the inner wall of the cannula. One or more points or a circumferential ring can be applied as follows: the flowable curable polymer material is applied in an appropriate arrangement to the inner wall of the cannula and then cured. Alternatively, a relatively large amount of the flowable curable polymer material can be applied to the inner wall of the cannula, the undesired material removed, and the material remaining on the inner wall of the cannula cured. The introduced material can also be cured first and the undesired material removed in a second step. For example, a circumferential ring on the inner wall of the cannula can first be cured, and then the internal diameter of the circumferential ring of cured material can then be adjusted to a desired dimension using a suitable tool, for example a stylet.

Alternatively, a solution of a cured polymer in a suitable solvent or a molten cured polymer can be used in the same way as for the curable polymer material, the curing step being replaced correspondingly by evaporation of the solvent or solidifying of the molten polymer. Examples of a solution are a customary rubber solution and the like, and examples of a melt are customary polymeric hot-melt adhesives.

The cured polymer is very especially an elastomeric polymer. Preferred examples of elastomeric polymers are silicone rubbers. Elastomeric polymers have proved to be especially advantageous in the present invention, because not only are they good in processing but also small amounts are well suited for firmly holding an implant in an injection cannula.

In a preferred embodiment of the method according to the invention the flowable physiologically tolerable material introduced into the cannula is distributed in the cannula before an implant is introduced into the cannula. For example, a semi-solid material can be uniformly distributed on the inner wall of the cannula, for example using a suitable tool, such as a stylet or the like.

In another preferred embodiment of the method according to the invention a portion of the flowable physiologically tolerable material introduced into the cannula is removed from the cannula again before the implant is introduced into the cannula. For example, undesired additional material can be removed from the cannula, for example, by using a stylet which allows only a gap of a defined width relative to the inner wall of the cannula. Accordingly, preferably a uniform thin layer of flowable physiologically tolerable material can be applied to the inner wall of the cannula. It is thus also possible to control in a simple way the maximum amount of flowable physiologically tolerable material introduced into the cannula.

As mentioned above, for example, a portion of a polymer material that has been introduced into the cannula and cured can be removed from the cannula again before the implant is introduced into the cannula. It is thus advantageously possible to utilise the good processing properties of customary curable polymer materials and/or the polymers obtainable therefrom. As a result, any arrangements of narrowed portions of the internal diameter of the cannula can readily be produced from polymers, preferably from elastomeric polymers.

In another especially preferred embodiment of the method according to the invention, an injection cannula having a lateral opening is used. Such injection cannulas are commercially available, for example under the designation "pencil point cannulas", for example from the company Süddeutsche Feinmechanik. A preferred cannula made of special steel with a luer-lock connecting system has a length of 32 mm, an external diameter of 1.6 mm and an internal diameter of 1.4 mm, an opening having a diameter of 1.2 mm being formed at a distance of 26 mm from the tip of the cannula. Such cannulas are already used for implant systems (see, for example, EP 1 716 883 A1 and DE 20 2009 016 524 U1, so that in the case of the present invention it is readily possible to use existing systems. The costs required for new development therefore do not arise.

The implant is, preferably, firmly held in the region of the lateral opening of the injection cannula. In this arrangement the lateral opening allows a simple visual check to be made for the presence of an implant in the cannula.

In an especially preferred development of the method according to the invention using an injection cannula having a lateral opening, the flowable physiologically tolerable material is introduced into the injection cannula through the lateral opening of the injection cannula. The lateral opening of the cannula allows easy access to the inner wall of the cannula in the region of the opening, so that the flowable physiologically tolerable material can easily be applied in a defined amount at a desired location on the inner wall of the cannula. As a result, it can advantageously be ensured that the implant is firmly held with a specific amount of material in the region of the lateral opening of the cannula. Preferably a droplet of the flowable physiologically tolerable material is applied to the inner wall of the cannula located opposite the opening. Special preference is given to the use of a semi-solid material. In an especially preferred embodiment, a droplet having a volume of 1 µl or less is applied to the inner wall of the cannula, more especially having a volume of from 0.1 to 0.9 µl, and very especially from 0.5 to 0.8 µl.

The implant preferably comprises an active ingredient selected from the group consisting of psychopharmaceuticals, especially antischizophrenics, such as, for example, risperidone, or peptides or proteins. An implant especially includes an active ingredient from the group of hormones or hormone antagonists and agonists, for example LHRH or LHRH antagonists, such as anastrozole. Also preferred are goserelin, leuprorelin and octreotide.

The implant preferably comprises a biologically degradable plastics material selected from the group consisting of polymers and copolymers of lactic acid and/or glycolic acid, especially polylactides und poly-lactide-co-glycolides, and also polyesters and lipids. Especially preferred implants comprise a plastics/active ingredient combination of poly-lactide-co-glycolide and goserelin.

The present invention also provides an injection cannula with implant, the implant being secured in the injection cannula using the method according to the invention. The injection cannula with implant according to the invention is distinguished by the fact that the implant is reliably held firmly when the cannula is moved, that is to say does not accidentally drop out of the cannula. When used as intended in combination with a suitable application device, the implant is easily injected out of the cannula into a patient by means of an applicator, for example a plunger.

In an especially preferred embodiment, the injection cannula with implant includes an implant which is detachably secured in a cannula having a lateral opening with a flowable physiologically tolerable material in the region of the opening on the inner wall of the cannula located opposite the opening. This cannula allows a simple visual check to be made for the presence of the implant.

The present invention will be described in more detail below by reference to examples, but the invention is not limited to these examples.

EXAMPLES

The following materials were used in the examples:

Injection cannula: special steel, silicone-coated, length 32 mm, internal diameter 1.4 mm, external diameter 1.6 mm with a lateral opening having a diameter of 1.2 mm at a distance of 26 mm from the tip of the cannula and a luer-lock connecting system, for example obtainable from the company SFM.

Implant: 15×1.5 mm made of 79.5%, by weight, poly-lactide-co-glycolide 50:50 and 20.5%, by weight, goserelin.

Semi-solid material: a mixture of polyethylene glycol which was prepared as follows: 1.23 g of PEG 400 and 1.23 g of PEG 1000 were melted together, with stirring, at 80° C. and, with further stirring, allowed to cool to room temperature. An ointment-like mass is formed. The production of PEG ointments by mixing various kinds of PEG is known to the person skilled in the art.

Curable polymer material: silicone rubber RTV-1, for example obtainable from the company Wacker Chemie under the brand name Elastosil E41.

Stylet: made of special steel, diameter 1.0 mm, for example obtainable from the company SFM.

Application system: see Example 6.

Example 1

A droplet of curable polymer material was introduced into an injection cannula in the region between the lateral opening and the luer-lock connecting system (above the opening or in the portion of the cannula remote from the tip). The curable polymer material was then distributed in the cannula using a stylet. The amount of polymer material introduced was determined as 10 mg by differential weighing. The polymer material was cured overnight. An implant was then introduced into the cannula from the luer-lock side and displaced using a stylet until it was located in the region of the lateral opening (visual inspection).

The implant could not be removed from the cannula by vigorous shaking. Using an application system it was possible to expel ("inject") the implant out of the cannula without problems, the expelled implant exhibiting no traces of silicone.

Example 2

Example 1 was repeated with the same result, but the amount of polymer material introduced was determined as 13 mg.

Example 3

A droplet of semi-solid material was introduced into an injection cannula in the region between the lateral opening and the tip of the cannula. The amount of semi-solid material introduced was determined as 4.2 mg by differential weighing. An implant was then introduced into the cannula from the luer-lock side. It was not necessary to use a filling aid (stylet).

Vigorous shaking did not cause the implant to drop out of the cannula. Using an application system it was possible to expel ("inject") the implant out of the cannula without problems, 4.1 mg of the semi-solid material being detected on the expelled implant by differential weighing.

Example 4

Example 3 was repeated with the same result, but the amount of semi-solid material introduced was determined as 5.6 mg, of which 5.0 mg were detected on the expelled implant.

Example 5

Example 3 was repeated with the same result, but the amount of semi-solid material introduced was reduced to 0.8 mg, of which 0.8 mg was detected on the expelled implant.

Example 6

A commercially available syringe (5 ml) was provided with a 0.9×40 mm cannula, the tip of which (bevel point) was removed with pincers in order to obtain a flat end, and filled with curable polymer material. Using this syringe a droplet of approximately 1 µl of the polymer material was introduced into an injection cannula on the inner wall of the cannula opposite from the lateral opening. The amount of polymer material introduced was determined as 1 mg by differential weighing. The polymer material was cured overnight. An implant was then introduced into the cannula from the luer-lock side and displaced using a stylet until it was located in the region of the lateral opening (visual inspection).

The implant could not be dislodged from the cannula by vigorous shaking. Using an application system it was possible to expel ("inject") the implant out of the cannula without problems, the expelled implant exhibiting no traces of silicone on the surface.

The invention claimed is:

1. A method for detachably securing an implant in an injection cannula comprising
   (a) introducing a physiologically tolerable material into an injection cannula, wherein the physiologically tolerable material comprises a curable polymer material,
   (b) distributing the physiologically tolerable material in the injection cannula when the physiologically tolerable material is flowable,
   (c) curing the physiologically tolerable material, and
   (d) introducing an implant into the injection cannula comprising the cured physiologically tolerable material, wherein the implant is in a form of a cylindrical rod comprising a plastic and active ingredient matrix and steps (a)-(d) are carried out prior to implantation into a patient.

2. The method of claim 1, wherein a portion of the physiologically tolerable material introduced into the injection cannula is removed from the injection cannula before introducing the implant into the injection cannula.

3. The method of claim 2, wherein the portion of the physiologically tolerable material is removed from the injection cannula before curing the physiologically tolerable material.

4. The method of claim 2, wherein the portion of the physiologically tolerable material is removed from the injection cannula after curing the physiologically tolerable material.

5. The method of claim 1, wherein the injection cannula has a lateral opening.

6. The method of claim 5, wherein the implant is detachably secured in a region of the lateral opening of the injection cannula.

7. The method of claim 6, wherein the physiologically tolerable material is introduced into the injection cannula through the lateral opening of the injection cannula.

8. The method of claim 1, wherein the implant comprises goserelin, leuprorelin, anastrozole, risperidone or octreotide.

9. The method of claim 1, wherein the implant comprises polymers or copolymers of lactic acid and/or glycolic acid.

10. An injection cannula comprising:
    an implant in the form of a cylindrical rod comprising a plastic and active ingredient matrix;
        wherein prior to implantation into a patient, the implant is detachably secured in the injection cannula by a physiologically tolerable material that is introduced into the injection cannula, the physiologically tolerable material comprises a curable polymer material,
        wherein prior to implantation into the patient, the physiologically tolerable material is distributed in the injection cannula when the physiologically tolerable material is flowable,
        wherein prior to implantation into the patient, the physiologically tolerable material is cured, and
        wherein prior to implantation into the patient, the implant is introduced into the injection cannula when the physiologically tolerable material is cured.

11. The injection cannula of claim 10, further comprising a lateral opening.

12. The injection cannula of claim 11, wherein the implant is detachably secured in the injection cannula via the physiologically tolerable material and wherein said implant is secured on an inner wall of the injection cannula that is opposite to the lateral opening of the injection cannula.

13. The injection cannula of claim 10 wherein the injection cannula is a customary injection cannula.

14. The injection cannula of claim 13 wherein the injection cannula comprises special steel.

15. The injection cannula of claim 14 wherein the injection cannula has a siliconized surface.

16. The injection cannula of claim 10, wherein the implant is detachably secured in the injection cannula over at least part of at least one longitudinal side of the injection cannula with the physiologically tolerable material.

17. The injection cannula of claim 16, wherein the implant is detachably secured in the injection cannula over up to 50% of the surface area of the at least one longitudinal side.

18. The injection cannula of claim 16, wherein the implant is detachably secured in the injection cannula over at least one point on the surface of at least one longitudinal side.

19. The injection cannula of claim 10, wherein the physiologically tolerable material has a layer thickness of from 0.1 to 1.2 mm.

20. The injection cannula of claim 11, wherein the implant is arranged in a region of the lateral opening of the injection cannula.

21. The injection cannula of claim 10, wherein the implant comprises goserelin, leuprorelin, anastrozole, risperidone or octreotide.

22. The injection cannula of claim 10, wherein the implant comprises polymers or copolymers of lactic acid and/or glycolic acid.

23. The injection cannula of claim 10, wherein the implant does not include any material identical to the physiologically tolerable material.

* * * * *